US012383646B2

(12) United States Patent
Heath et al.

(10) Patent No.: US 12,383,646 B2
(45) Date of Patent: Aug. 12, 2025

(54) HYPOCHLORITE COMPOSITIONS, METHODS OF MANUFACTURE AND USES THEREOF

(71) Applicant: BONDS CHEMICALS PTY LTD, Victoria (AU)

(72) Inventors: Campbell Heath, Victoria (AU); Maxwell Bradbury, Victoria (AU)

(73) Assignee: BONDS CHEMICALS PTY LTD, Victoria (AU)

(*) Notice: Subject to any disclaimer, the term of this patent is extended or adjusted under 35 U.S.C. 154(b) by 676 days.

(21) Appl. No.: 17/764,940

(22) PCT Filed: Sep. 30, 2020

(86) PCT No.: PCT/AU2020/051038
§ 371 (c)(1),
(2) Date: Mar. 29, 2022

(87) PCT Pub. No.: WO2021/062467
PCT Pub. Date: Apr. 8, 2021

(65) Prior Publication Data
US 2022/0371927 A1    Nov. 24, 2022

(30) Foreign Application Priority Data
Sep. 30, 2019  (AU) .................. 2019903679
Apr. 1, 2020   (AU) .................. 2020100501

(51) Int. Cl.
A61L 2/23   (2006.01)
A01N 25/02  (2006.01)
A01N 59/08  (2006.01)
A61L 2/26   (2006.01)
C02F 1/00   (2023.01)
(Continued)

(52) U.S. Cl.
CPC ............... *A61L 2/23* (2013.01); *A01N 25/02* (2013.01); *A01N 59/08* (2013.01); *A61L 2/26* (2013.01); *C02F 1/001* (2013.01); *C02F 1/687* (2013.01); *C02F 1/688* (2013.01); *C02F 1/76* (2013.01);
(Continued)

(58) Field of Classification Search
CPC ...... C02F 1/68; C02F 1/00; A61L 2/26; A61L 2/23; A01N 25/02; A01N 59/08
See application file for complete search history.

(56) References Cited

U.S. PATENT DOCUMENTS 1,383,224 A   6/1921   MacMillan
3,793,216 A * 2/1974  Dychdala ............... C02F 1/76
                                                  423/474
(Continued)

FOREIGN PATENT DOCUMENTS

CN   1120391 A  *  4/1996
CN   103408125 A    11/2013
(Continued)

OTHER PUBLICATIONS

DE-102009025654-A1 Translation (Year: 2010).*
(Continued)

*Primary Examiner* — Clare M Perrin
(74) *Attorney, Agent, or Firm* — BLANK ROME LLP

(57) ABSTRACT

The present invention relates to a family of very stable aqueous hypochlorite products and methods for reducing the self reactivity of $Ca(OCl)_2$.

15 Claims, 13 Drawing Sheets

(51) Int. Cl.
*C02F 1/68* (2023.01)
*C02F 1/76* (2023.01)
*A61L 101/06* (2006.01)
*C02F 103/42* (2006.01)

(52) U.S. Cl.
CPC ....... *A61L 2101/06* (2020.08); *C02F 2103/42* (2013.01); *C02F 2303/04* (2013.01)

(56) References Cited

U.S. PATENT DOCUMENTS

| | | | | |
|---|---|---|---|---|
| 4,276,349 | A * | 6/1981 | Saeman | C01B 11/068 |
| | | | | 423/474 |
| 4,689,169 | A * | 8/1987 | Mason | A01N 59/00 |
| | | | | 426/316 |
| 4,965,016 | A | 10/1990 | Saitoh et al. | |
| 2005/0279971 | A1 | 12/2005 | Garris | |
| 2007/0125979 | A1 * | 6/2007 | Lei | C02F 1/76 |
| | | | | 423/474 |
| 2007/0224108 | A1 * | 9/2007 | Garris | A01N 59/00 |
| | | | | 423/474 |
| 2010/0080857 | A1 * | 4/2010 | Pickens | A01N 59/14 |
| | | | | 424/665 |
| 2011/0052724 | A1 * | 3/2011 | Pickens | A01N 59/06 |
| | | | | 424/665 |
| 2011/0052726 | A1 | 3/2011 | Smith et al. | |
| 2014/0263020 | A1 * | 9/2014 | MacDonald | C02F 1/003 |
| | | | | 210/232 |
| 2021/0120823 | A1 * | 4/2021 | Shiao | A01N 59/00 |

FOREIGN PATENT DOCUMENTS

| | | | | |
|---|---|---|---|---|
| DE | 102009025654 | A1 * | 12/2010 | ................ E02F 3/88 |
| FR | 2304567 | A1 | 10/1976 | |
| GB | 190215261 | A | 10/1902 | |
| GB | 2116040 | A | 9/1983 | |
| WO | WO-2014108767 | A1 * | 7/2014 | ............. A01N 25/08 |
| WO | WO-2016038449 | A1 * | 3/2016 | ............. A01N 25/34 |

OTHER PUBLICATIONS

Machine translation of CN-1120391-A, pp. 1-5. (Year: 1996).*
Redox—Safety Data Sheet—Calcium Hypochlorite, Hydrated [retrieved from internet on Dec. 2, 2020], <URL: http://docs.redox.com/sds/4973.Pdf>, published on Jun. 17, 2015, p. 3.
Redox Safety Data Sheet Calcium hypochlorite, hydrated (UN2880), Revision 5, Sep. 17, 2019.

* cited by examiner

Figure 8

Comparison between hypochlorite solutions made using different processes

Compare CAPEX + OPEX costs for various alternatives

| Distance from East Coast Capital | 0 | 100 | 200 | 300 | 400 | 500 | 600 | 800 | 900 | 1000 |
|---|---|---|---|---|---|---|---|---|---|---|
| | \multicolumn{10}{c}{OPEX + CAPEX (AUD/kg of Chlorine equivalent)} | | | | | | | | | |
| Metathesis | 2.070893 | 2.240083 | 2.240083 | 2.240083 | 2.240083 | 2.240083 | 2.240083 | 2.240083 | 2.240083 | 2.240083 |
| Chlorination at site (Boal numbers) | 2.340801 | 2.386331 | 2.391371 | 2.396401 | 2.401441 | 2.406471 | 2.411511 | 2.421581 | 2.426611 | 2.431651 |
| CAP NaOCl delivered 12.5% Tra | 2.064553 | 2.488893 | 2.535866 | 2.582745 | 2.629718 | 2.676598 | 2.723577 | 2.817423 | 2.864302 | 2.911275 |
| Avg OSG | 2.53722 | 2.651045 | 2.663645 | 2.67622 | 2.68882 | 2.701395 | 2.713995 | 2.73917 | 2.751745 | 2.764345 |

Notes:—  Capex is depreciated over 20 years
OSG costs were extracted from Hazen and Sawyer
CAP NaOCl costs were extracted from Hazen and Sawyer
Costs for chlorination at site were taken from Boal.

Figure 9

The economics associate with drinking water chlorination

Figure 10

Results of Stoichiometric mixture with brake fluid & UN Protocol

HYPOCHLORITE COMPOSITIONS, METHODS OF MANUFACTURE AND USES THEREOF

FIELD

The present invention relates to a family of very stable aqueous hypochlorite products and methods for reducing the self reactivity of $Ca(OCl)_2$.

BACKGROUND

Abbreviations

OSG=On Site Generator by CAP process.
CAP=ChlorAlkali Process
HSLS=High Strength Low Salt sodium hypochlorite belonging to Powell Manufacturing.
HRL=Highest Recommended Level
HAL=Highest Allowable Level
CAPEX=Capital Expenditure
OPEX=Operating Expenditure
ADMIX=Intimately and physically mixed reactant crystalline solids in stoichiometric proportions suitable for use as a metathesis feedstock for producing an alkali metal hypochlorite.
PCM=Phase Change Material.
RESIDUAL IONIC STRENGTH (RI)=
RI=Total Ionic Strength ($I_T$)–[Ionic strength of Hypochlorite species]
COATED=A crystalline solid (calcium hypochlorite) that has been sprayed with a solution containing a solvent (water) and a dissolved coating material (hydrated alkali metal salt) and then partially dried to remove some of the solvent (water).
SALT METATHESIS=a reaction between two inorganic salts where one product is insoluble in water. The reactants need not be highly soluble for the reaction to take place, but may take a longer time for the reaction to reach completion.

Drinking water sterilization has traditionally been achieved using chlorination via liquefied chlorine gas delivered in bulk, drums, or cylinders. Transporting and handling large volumes of liquefied chlorine gas is an ongoing safety issue, and to solve this problem water treatment plants have been transitioning to using bulk CAP aqueous sodium hypochlorite (12.5% w/w).

Hypochlorites are very effective, cheap sanitizers which provide a valuable disinfection service to humanity. The largest use for hypochlorite is for drinking water sterilization. Its use for this application however has been hindered due to its low strength; CAP sodium hypochlorite (12.5% w/w) is mostly composed of water, and is thus expensive to transport at scale. Some plants have installed sodium hypochlorite OSGs to reduce the transport cost, and Powell has developed a HSLS process to make a more concentrated CAP sodium hypochlorite (30% w/w). At this time the HSLS process, in theory, can produce the most stable aqueous hypochlorite with the resultant lowest disproportionation rate to chlorate and perchlorate. The disadvantages of the HSLS process are:—

1.1 The OPEX and CAPEX required.
1.2 The need to locate the process adjacent to a chlorine plant or alternatively to continue transporting liquefied chlorine gas in bulk, drums or cylinders to the manufacturing site.
1.3 The continuing transport cost of 30% w/w sodium hypochlorite. (70% water, and a Dangerous Good.)

All aqueous hypochlorites are unstable and disproportionate into undesirable chlorates and perchlorates. Instability increases with an increase in hypochlorite concentration. Upon heating, exposure to UV light or simply storage overtime, hypochlorite will disproportionate to a mixture of chloride, oxygen, chlorates and perchlorates:

$$2ClO^- \rightarrow 2Cl^- + O_2$$

$$3ClO^- \rightarrow 2Cl^- + ClO_3^-$$

$$OCl^- + ClO_3^{2-} \rightarrow ClO_4^- + Cl^-$$

Recently, as a result of improved analytical capability, perchlorates derived from hypochlorite have been shown to be a major human health issue. Perchlorate has been found to both interfere with brain development in children and present a dose-related risk to iodine uptake in healthy adults, as an endocrine disruptor of the human thyroid system. Perchlorate contamination of drinking water is a major global concern and the US EPA has recently proposed (in 2018) to regulate the perchlorate level in drinking water via a maximum contaminant level goal [MCLG]. Currently the US EPA has levels for drinking water set at:—

| HRL | Chlorate: | 210 | µg/L |
| HAL | Perchlorate: | 15 | µg/L |

Whilst the limit set by The World Health Organization is 70 µg/L for chlorate (2016).

To ameliorate this issue, the current practice is focused on better management techniques and guidelines for handling and storing hypochlorite to prevent disproportionation. For example, some of the key recommendations are to dilute hypochlorite solutions on delivery since halving the concentration decreases the disproportionation rate by a factor of 7, to store hypochlorite solutions at lower temperatures as reducing temperature by 5° C. decreases disproportionation rate by a factor of 2, to keep the pH between 11 and 13 even after dilution, and importantly, to avoid extended storage times by, using fresh hypochlorite solutions when possible.

The most common aqueous hypochlorite is sodium hypochlorite which is made by the Chlor Alkali Process (CAP) shown by reaction (I)

$$Cl_2 + 2NaOH = NaOCl + NaCl + H_2O (CAP) \tag{I}$$

Another method for aqueous hypochlorite preparation is by salt metathesis reactions such as:—

$$Ca(OCl)_2 + Na_2CO_3 = 2NaOCl + CaCO_3 \tag{II}$$

$$Ca(OCl)_2 + Na_2SO_4 = 2NaOCl + CaSO_4 \tag{III}$$

Although the preparation of aqueous hypochlorites by metathesis has been known for many decades, the process has never achieved commercial success. The lack of application is due to the fact that Chlor Alkali Plants (CAP) must produce aqueous hypochlorite as a by-product.

As the demand for chlorine has increased (eg PVC manufacture), in turn producing more CAP hypochlorite, aqueous hypochlorite produced by metathesis has not been required, and hence this process has never been developed or commercialized.

Also as bleaching activity increased, emphasis was placed upon the development of solid hypochlorites to avoid the costly transport of water which is the main component of sodium hypochlorite.

Only lithium hypochlorite, calcium hypochlorite and barium hypochlorite have been isolated as pure anhydrous solids.

Processes for the manufacture of solid calcium hypochlorite have been in development since the early 1950's, and today there ae two main processes:—

A) The sodium process based on the following reaction:—

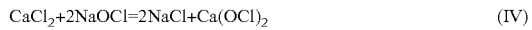
$$CaCl_2 + 2NaOCl = 2NaCl + Ca(OCl)_2 \qquad (IV)$$

B) The calcium process based on the reaction:—

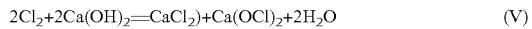
$$2Cl_2 + 2Ca(OH)_2 = CaCl_2 + Ca(OCl)_2 + 2H_2O \qquad (V)$$

Both processes are widely used, although product from the sodium process seems to be dominant in the market.

A major problem with the use of solid calcium hypochlorite is storage and handling of large quantities because of its self reactivity.

It is well known that if a single drop of organic liquid such as glycerin or brake fluid were to fall into a drum of solid calcium hypochlorite it can start an exothermic decomposition causing the whole contents to heat up and bubble like boiling porridge.

There have been numerous fatalities and fires on board ships which have been carrying large quantities of solid calcium hypochlorite in plastic lined steel drums.

The disproportionation reaction of solid by a hydration reaction is exothermic and in the case of concentrated solid hypochlorites, such as LiOCl and $Ca(OCl)_2$, can lead to dangerous thermal runaway reactions and potentially explosions. As a result, solid hypochlorite is classified as a dangerous good by the criteria of the Australian Dangerous Goods Code (ADG Code) for Transport by Road and Rail. This makes it expensive to transport and store large quantities of solid hypochlorite as many safety precautions must be followed. To further mitigate the risk of fire caused by the self reactivity of calcium hypochlorite on ships, government authorities rely on standard tests performed under the UN Protocol or the US NFPA to classify into different risk categories, calcium hypochlorite depending on its strength, degree of hydration and diluent concentrations.

In addition to the production of excess CAP hypochlorite, restrictive regulations associated with the storage, transport and handling of calcium hypochlorite have increased the cost of its use for water treatment and these reasons have prevented the material from being used as a metathesis feedstock.

Considerable work has been done over the last 50 years to find a way to reduce the self reactivity of solid $Ca(OCl)_2$. The following methods have been investigated:—

1 Maintaining a level of moisture in the $Ca(OCl)_2$
2 Reducing the available chlorine level in the product
3 Adding non hydrated diluents to the product
4 Coating the product with hydroscopic materials There is an urgent need to be able to produce, at the point of use, a more stable aqueous hypochlorite with less generation of chlorates and perchlorates. Further, if production of aqueous hypochlorite by metathesis is to become an industrial process, large quantities of calcium hypochlorite must be able to be transported and stored in a safe manner.

SUMMARY

The present disclosure is predicated on the discovery that certain solid hypochlorite admixes are advantageous for storing, transportation and use. In particular, and without being bound by theory, the inventors have found that the addition of particular quantities of particular phase change material (PCM) to solid calcium hypochlorite serves a triple purpose:—

(1) reducing calcium hypochlorite's self-reactivity.
(2) acting as a feed material for a salt metathesis reaction, and
(3) acting as a partial source of water for the salt metathesis reaction to take place.

The presently described admixes have been found to have the following advantageous qualities:

1 A stoichiometric admix with reduced self-reactivity of $Ca(OCl)_2$ below that of a 5.1 oxidizer meaning that the admix will be safe to transport and handle.
2 The stoichiometric admix can be retailed as a powder in a soluble sachet or as a tablet wrapped in a soluble material, similar to dishwashing tablets.
3 Since the stoichiometric admix is a non 5.1 oxidizer, it is safer for storage in retail outlets and the domestic environment.
4 The stoichiometric admix used as a metathesis feedstock is the only known way of storing sodium hypochlorite without significant product (NaOCl) degradation.
5 Lower Chlorates and Perchlorates makes metathesized hypochlorites safer to use in Dairy CIP cleaning. Similarly, they are safer to use as bleach washes for fruit and vegetable, for commercial and domestic cleaning, and for pools and spas (hot tubs).
6 Lower Chlorates and Perchlorates are also an advantage for drinking water chlorination. Chlorination using the metathesis process described herein is also the cheapest method for drinking water treatment. (see Table 3).
7 Hypochlorites made via the present metathesis process have better high temperature stability than other comparable hypochlorites, making them especially suitable for use in spas (hot tubs).
8 Since metathesis hypochlorites are more stable than conventional hypochlorites, they have superior time based efficacy.
9 Potassium and sodium based metathesized hypochlorites containing exceedingly low caustic levels (which is only added to the hypochlorite as a stability booster) are environmentally friendly spa sanitisers. [Caustic levels in conventional hypochlorites prevent their use in spas (hot tubs) because of corrosion to spa (hot tub) surfaces.].

Accordingly, the resultant aqueous sodium hypochlorite produced by metathesis can be formed easily and cheaply by the safe storage and handling of the solid reactant admixed blend, while the aqueous concentration of the chlorate and/or perchlorate by-products are reduced to a previously un-achievable minimal level.

The inventors have found, for the first time, that by increasing, for example, the concentration of certain PCM in the admix from about 55% w/w to about 70% w/w, the reactivity is further downgraded from a 5.1 oxidizer to one that is even less reactive, and at the same time is suitable for use as a metathesis feed. This also allows calcium hypochlorite to be safely used in large amounts as a metathesis feedstock.

Typically the PCM is a hydrated sodium salt that has a phase transition temperature of about 19° C. to 70° C., and a heat of fusion of about 150 kJ/kg to about 280 kJ/kg.

Accordingly, in one aspect the present invention relates to an uncoated admix comprising:

a) calcium hypochlorite (Ca(OCl)$_2$) having an available chlorine content of from 65-80% and a water content of about 4% to about 10% w/w; and
b) a hydrated phase change material (PCM);
wherein the Ca(OCl)$_2$ and phase change material are physically and intimately mixed as a solid crystalline form in approximately stoichiometric proportions to form a tablet or a granular mix of solids;
wherein the hydrated phase change material is a hydrated alkali metal salt selected from hydrated Na$_2$CO$_3$, hydrated Na$_2$SO$_4$, hydrated Na$_3$PO$_4$, hydrated NaHCO$_3$, hydrated NaHSO$_4$, hydrated Na$_2$HPO$_4$ or hydrated NaH$_2$PO$_4$; and
wherein total water comprises about 30% w/w to about 45% w/w of the uncoated admix;
wherein the hydrated phase change material as defined by b) comprises about 55% w/w to about 70% w/w of the uncoated admix;
wherein the Ca(OCl)$_2$ as defined by a) comprises about 35% w/w to about 45% w/w of the uncoated admix;
wherein the uncoated admix has an available chlorine content of from 20-35%; and wherein the uncoated admix is react-able in water to form a sodium hypochlorite solution with a concentration of less than 15% w/v and a salt.

The uncoated admixes defined above are advantageously classified as non Division 5.1 oxidizers. That is, one of the advantages of the present invention over admixes currently reported, is that they do not require an additional coating or encapsulation in order to achieve the desired stability as disclosed herein. Also, as used herein, 'uncoated' refers to the admix (Ca(OCl)$_2$ and phase change material) which does not have an evaporated layer of hydrated alkali metal salt on the surface of the Ca(OCl)$_2$.

The skilled person would appreciate that the level of water in the admix (prior to reaction in water) is mostly dependent on the amount of water in the Ca(OCl)$_2$ feedstock and the amount in the hydrated PCM. For instance, in certain embodiments, at least about 4 to 10% w/w of water could be found in the Ca(OCl)$_2$ feedstock. For instance, about 4%, 5%, 6%, 7%, 8%, 9% or about 10% of water in the Ca(OCl)$_2$) measured on a % wt/wt basis. The water content of Ca(OCl)$_2$ is carefully controlled to prevent self-reactivity. If it is too dry, the dust becomes a dust explosion hazard. At a critical amount of water Ca(OCl)$_2$ self reacts because there is insufficient water to quench the exothermic heat of reaction. At a water content above the critical level, the exotherm does not develop enough heat to sustain a runaway self-reaction.

The Ca(OCl)$_2$ feedstock used in the present admixes is also characterised with a high available chlorine content of from 65-80%, preferably about 70%, 71%, 72%, 73%, 74%, 75%, or about 76%.

The present invention also relates to a sodium hypochlorite solution produced from the uncoated admix, the sodium hypochlorite solution having a half-life of about 1.4 to about 1.7 times than that of Chlor Alkali Plant (CAP) hypochlorites under the same conditions of concentration, temperature profile, exposure to light, storage time and container material; the sodium hypochlorite solution having a chlorate concentration at least 25% less than that of CAP hypochlorites under the same conditions of concentration, temperature profile, exposure to light, storage time and container material;
the sodium hypochlorite solution having a perchlorate concentration at least 50% less than that of CAP hypochlorites under the same conditions of concentration, temperature profile, exposure to light, storage time and container material;
the sodium hypochlorite solution having a residual ionic concentration of less than 1.7 g moles/litre and preferably about 0.2 g moles/litre; and
the sodium hypochlorite solution having an available chlorine concentration of about 100 g/l to about 160 g/l.

The inventors have also found that by reacting a certain non-hydrated alkali metal salts, of sodium, lithium or a potassium with Ca(OCl)$_2$-via a metathesis reaction in stoichiometric proportions, a hypochlorite solution can be obtained with an extremely low soluble by-product concentration.

Accordingly, in another aspect the invention provides a hypochlorite solution produced by a reaction of calcium hypochlorite (having an available chlorine content of from 65-80% and a water content of about 4% to about 10% w/w) with a non-hydrated alkali metal salt; wherein the calcium hypochlorite and the non-hydrated alkali metal salt are in approximately stoichiometric proportions;
wherein an anion associated with the non-hydrated alkali metal salt is selected from $CO_3^{2-}$, $SO_4^{2-}$, $PO_4^{3-}$, $HPO_4^{2-}$, $H_2PO_4^-$, $OH^-$, $SO_3^{2-}$, $HSO_4^-$, $HSO_3^-$ and $S_2O_3^{2-}$;
the hypochlorite solution having a half-life about 1.4 to about 1.7 times than that of Chlor Alkali Plant (CAP) hypochlorites under the same conditions of concentration, temperature profile, exposure to light, storage time and container material;
the hypochlorite solution having a chlorate concentration at least 25% less than that of CAP hypochlorites under the same conditions of concentration, temperature profile, exposure to light, storage time and container material;
the hypochlorite solution having a perchlorate concentration at least 50% less than that of CAP hypochlorites under the same conditions of concentration, temperature profile, exposure to light, storage time and container material;
the hypochlorite solution having a residual ionic concentration of less than 1.7 g moles/litre and preferably about 0.2 g moles/litre; and
the hypochlorite solution having an available chlorine concentration of about 100 g/l to about 160 g/l.

In some embodiments, if the calcium hypochlorite is produced from a reaction of chlorine and calcium hydroxide (calcium process, reaction V), the sodium hypochlorite solution or hypochlorite solution can have a half-life about 20% to about 50% more than that of a hypochlorite solution produced from a reaction of calcium hypochlorite produced by reacting calcium chloride and sodium hypochlorite (sodium process, reaction IV).

In other embodiments, the sodium hypochlorite solution or hypochlorite solution further comprises a soluble alkali of about 0.1 g/L to about 0.5 g/L, and optionally an alkaline buffer selected from carbonate, bicarbonate or a mixture thereof; and
wherein the sodium hypochlorite solution or hypochlorite solution is produced via a metathesis reaction.

BRIEF DESCRIPTION OF THE DRAWINGS

Embodiments of the present invention will now be described, by way of non-limiting example, with reference to the drawings in which:

FIG. 8 a table which compares hypochlorite solutions made using different processes.

FIG. 9 a table showing the economics associated with drinking water chlorination.

FIG. 10 a table showing the results of stoichiometric mixture with brake fluid and UN protocol.

DETAILED DESCRIPTION

Figure 1:
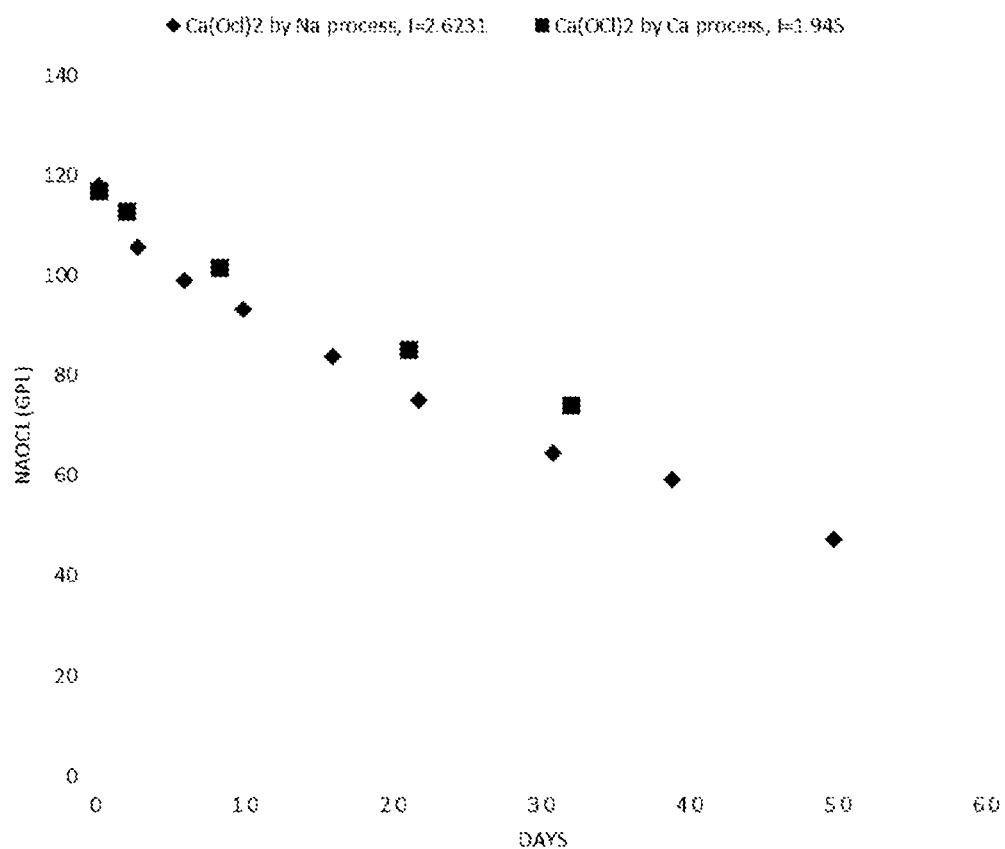
FIG. 1 illustrates a comparison of NaOCl stabilities made by metathesis reaction with two different calcium hypochlorites. (one made by Na process, the other by the Ca process).

In one aspect, the present invention is predicated on the discovery that the reactivity of solid calcium hypochlorite can be reduced by mixing, at least in stoichiometric proportion, with a hydrated alkali metal salt (a phase change material (PCM)). When mixed with water, such resultant hypochlorite product is more stable than CAP and HSLS (by Powell) hypochlorites, and has a residual ionic concentration less than 1.7 g·mole/litre and as low as 0.2 g mole/litre. Advantageously, the solid calcium hypochlorite admixes have a lower oxidizer classification than calcium hypochlorite alone, which facilitates its safe transportation and storage.

To solve the problem of the safe transportation and storage of calcium hypochlorite, the inventors have developed an uncoated admix composition which allows for a new way to safely handle raw materials for the salt metathesis reaction.

Accordingly, the present disclosure also relates to a admix comprising:
  a) calcium hypochlorite having an available chlorine content of from 65-80% and a water content of about 4% to about 10% w/w; and
  b) a hydrated phase change material (PCM);
  wherein the admix is in a solid form,
  wherein the phase change material is a hydrated alkali metal salt selected from hydrated $Na_2CO_3$, hydrated $Na_2SO_4$, hydrated $Na_3PO_4$, hydrated $NaHCO_3$, hydrated $NaHSO_4$, hydrated $Na_2HPO_4$ or hydrated $NaH_2PO_4$;
  wherein the phase change material and the calcium hypochlorite are mixed in approximately stoichiometric proportions; and
  wherein the weight ratio of total water (for instance, approximately 10% $H_2O$ in $Ca(OCl)_2$+$H_2O$ in PCM) to the admix is about 30% w/w to about 45% w/w;
  wherein the hydrated phase change material is about 55% w/w to about 70% w/w of the admix; and
  wherein the admix is react-able in water to form a sodium hypochlorite solution and a salt.

Advantageously, the metathesis process can allow for the preparation of fresh hypochlorites (family includes Na, Li, and K) at the point of use.

The water present in the admix includes water that is chemically bonded and/or free. This water includes water of hydration, which is water that is stoichiometrically bound in a crystal. The water can be chemically bonded via hydrogen bonding. In some embodiments, the weight ratio of total water ($H_2O$ in PCM+approximately for example 4% to 10% $H_2O$ in $Ca(OCl)_2$) to the admix is about 30% w/w to about 45% w/w, about 30% w/w to about 40% w/w, or about 35% w/w to about 40% w/w.

Advantageously, the phase change material and the calcium hypochlorite are mixed in approximately stoichiometric proportions (for instance about 1:1) which allows for calcium hypochlorite to be downgraded from a 5.1 oxidizer to one which is less reactive. This allows for easy compliance with legislated requirements for the safe storage and transport of dangerous goods as compared to pure $Ca(OCl)_2$ feedstock alone. The admix may also be more safely distributed and stored for retail and wholesale markets as metathesis feedstock. In addition to acting as a heat sink, the phase change material is also a feed material for a salt metathesis reaction to convert the calcium hypochlorite to a very pure sodium hypochlorite. Further, the hydrated phase change material provides a source of water for the salt metathesis reaction. Salt metathesis reactions can be tailored to go to completion by the choice of very insoluble products of a reactants and contaminants, and by eliminating excess reactants. In this regard, the supply chain logistics (storage, transport and handling) are safer and simplified to allow calcium hypochlorite to be used as a metathesis feedstock.

Hazard class 5 oxidizers are defined as materials that can start and support a fire through the chemical reaction of oxidation. A subset of class 5 oxidizers are 5.1 oxidizers. 5.1 oxidizers refers to a material that may, generally by yielding oxygen, cause or enhance the combustion of other materials. A solid material is classed as a Division 5.1 material if, when tested in accordance with the UN Manual of Tests and Criteria, its mean burning time is less than or equal to the burning time of a 3:7 potassium bromate/cellulose mixture. A material is classed as a Division 5.1 material if, when tested in accordance with the UN Manual of Tests and Criteria, it spontaneously ignites or its mean time for a pressure rise from 690 kPa to 2070 kPa gauge is less than the time of a 1:1 nitric acid (65%)/cellulose mixture.

In some embodiments, the weight ratio of calcium hypochlorite (including up to about 10% $H_2O$) to the uncoated admix is about 35% w/w to about 45% w/w. In other embodiments, the damp (approximately up to 10% $H_2O$) calcium hypochlorite is about 40% w/w to about 60% w/w, about 40% w/w to about 55% w/w, about 45% w/w to about 55% w/w or about 45% w/w to about 50% w/w.

Because diluents and PCM's are biologically inactive, they reduce the efficacy of the treated $Ca(OCl)_2$ admix, as a result, manufacturers and patent holders have restricted the amount of these materials they include in the admix to less than 40% w/w.

In contrast the present invention uses the selected hydrated PCM's in an amount greater than about 55% w/w of the total admix, the PCM reduces the self reactivity of calcium hypochlorite to a greater extent whilst serving as a reactant for a salt metathesis reaction.

The phase change material contains water in its hydrated form and acts as a heat sink with its high latent heat of fusion, and also acts as reactant.

Accordingly, in some embodiments, the weight ratio of the hydrated phase change material to the admix is more than 55% w/w to about 70% w/w of the admix, or about 60% w/w to about 70% w/w, or about 65% w/w to about 70% w/w. In other embodiments, the hydrated PCM is about 55% w/w to about 60% w/w, about 55% w/w to about 65% w/w, or about 55% w/w to about 70% w/w.

In some embodiments, the $Ca(OCl)_2$ and phase change material are in approximately stoichiometric proportions. In this regard, either the $Ca(OCl)_2$ or the phase change material can be in slight excess. For example, the stoichiometric equivalence ratio of $Ca(OCl)_2$ to phase change material (such as hydrated $Na_2CO_3$, hydrated $Na_2SO_4$, hydrated $NaHCO_3$, hydrated $NaHSO_4$) can be 0.9:1, 1:1, 1.1:1, 1:0.9, or 1:1.1. The stoichiometric equivalence ratio of $Ca(OCl)_2$ to phase change material (such as hydrated $Na_3PO_4$, hydrated $Na_2HPO_4$ or hydrated $NaH_2PO_4$) can be 2.9:2, 3:2, 3.1:2, 3:1.9, or 3:2.1.

In some embodiments, the stoichiometric equivalence ratio of the phase change material to calcium hypochlorite is from 1:1 to about 1.5:1. In other embodiments, the stoichiometric ratio is about 1.4:1 to about 1:1, about 1.3:1 to about 1:1, about 1.2:1 to about 1:1 or about 1.1:1 to about 1:1.

In some embodiments, the stoichiometric ratio of phase change material to calcium hypochlorite is about 1:1 to about 1:1.5. In other embodiments, the stoichiometric ratio is about 1:1 to about 1:1.4, about 1:1 to about 1:1.3, about 1:1 to about 1:1.2 or about 1:1 to about 1:1.1.

In some embodiments, the phase change material has a heat of fusion of about 150 kJ/kg to about 280 kJ/kg. In other embodiments, the heat of fusion is about 160 kJ/kg to about 280 kJ/kg, about 170 kJ/kg to about 280 kJ/kg, about 180 kJ/kg to about 280 kJ/kg, about 190 kJ/kg to about 280 kJ/kg or about 200 kJ/kg to about 280 kJ/kg In other embodiments, the phase change material has a phase transition temperature of about 19° C. to about 70° C. In this regard, the 'phase transition temperature' is the temperature at which a change of state occurs, resulting in a transition of that state to another state. For example, the phase transition can be from one solid phase (crystal structure) to another solid phase (crystal structure) or to a liquid phase. In other embodiments, the phase transition temperature is about 25° C. to about 70° C., about 30° C. to about 70° C., about 40° C. to about 70° C. or about 50° C. to about 70° C.

In other embodiments, wherein the phase change material is selected from $Na_2CO_3 \cdot 10H_2O$, $Na_2SO_4 \cdot 10H_2O$ or $Na_3PO_4 \cdot 12H_2O$.

When the composition is added to water, the following metathesis reactions occur:

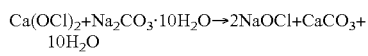
$Ca(OCl)_2 + Na_2CO_3 \cdot 10H_2O \rightarrow 2NaOCl + CaCO_3 + 10H_2O$

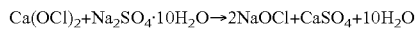
$Ca(OCl)_2 + Na_2SO_4 \cdot 10H_2O \rightarrow 2NaOCl + CaSO_4 + 10H_2O$

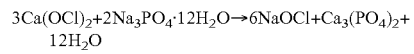
$3Ca(OCl)_2 + 2Na_3PO_4 \cdot 12H_2O \rightarrow 6NaOCl + Ca_3(PO_4)_2 + 12H_2O$ Advantageously, as opposed to hydrated magnesium sulphate, commonly reported in the literature, these PCM's do not add to the hardness of the water system that the $Ca(OCl)_2$ is being used to treat. Accordingly, this results in the water system (for example of a swimming pool) that is clean and sparkling.

Further, due to the low solubility of calcium by-products such as $CaCO_3$, $Ca_2SO_4$ and $Ca_3(PO_4)_2$, these insoluble salts can be removed, further improving the purity of the hypochlorite solution. A device fitted with a filtration means for removing such by-products is described further below which can be used to dispense the admix into a body of water (such as a pool or spa (hot tub)) in order to effect a metathesis reaction and generate sodium hypochlorite in situ.

In other embodiments, the sodium hypochlorite solution is characterised by a lower chlorate concentration governed by the total ionic concentration but more particularly by a residual ionic concentration of less than 1.7 M, down to about 0.2 M.

The chlorate content will still be dependent upon time, temperature history, strength of the hypochlorite solution and starting chlorate concentration, but will always be less than CAP hypochlorite and, in some instances, HSLS hypochlorites because of the advantage of the lowest residual ionic strength.

In other embodiments the sodium hypochlorite solution is characterised by a lower perchlorate concentration governed by the total ionic concentration but more particularly by the residual ionic concentration of less than 1.7 M, down to about 0.2 M The perchlorate content will still be dependent upon time, temperature history, strength of the hypochlorite solution and starting perchlorate concentration, but will always be less than CAP hypochlorite and, in some instances, HSLS hypochlorites because of the advantage of the lowest residual ionic strength.

In other embodiments, the admix is provided as a tablet or a granular mix of solids. The admix is physically and intimately mixed as a solid crystalline form.

To solve the problem of high generation of chlorates and perchlorates in CAP hypochlorates, the inventors have discovered a new family of extremely stable aqueous hypochlorite products made by a salt metathesis process.

In an aspect, the present invention provides a family of extremely stable aqueous hypochlorite products including Na, K, and Li which have a residual ionic strength of less than 1.7 M.

The stability and rate of disproportionation of aqueous hypochlorites is markedly dependent on the concentration of the hypochlorite molecules in solution. In order to understand the impact of impurities upon hypochlorite stability it is necessary to devise a way of removing hypochlorite concentration from consideration. This was done by comparing hypochlorites based on their residual ionic strengths instead of the conventional total ionic strength. As a result, it was discovered that the stability of hypochlorites could be reliably indicated by calculating their residual ionic strengths. (or calculating from experimental measurements) Furthermore, for the first time, it was found that residual ionic strength was a quantitative method of defining a family of hypochlorite products that are markedly different (greater stability) to standard CAP hypochlorite which has a residual ionic strength greater than about 1.7 M.

Residual ionic strength (RI) is first defined.

Aqueous hypochlorites are difficult to describe as they have variable parameters such as:—
1. Metallic parent, (Ca, Ba, Mg, Na, K, and Li)
2. Strength, which may be measured as gpl of available chlorine
3. Method of preparation (CAP and Salt Metathesis)
4. Impurities, e.g. NaCl, CaCl$_2$), heavy metals etc.

An important parameter influencing the stability of an aqueous hypochlorite is its ionic strength. The Total Ionic strength for aqueous alkali metal hypochlorites is expressed as $$I_T = \tfrac{1}{2}\Sigma m_i z_i^2 = \tfrac{1}{2}(m_1 z_1^2 + m_2 z_2^2 + \ldots + m_n z_n^2) \text{ where} \quad (VI)$$

n=total number of different ionic species in solution
m=molal concentration, in this case molar.
z=Charge on the ion of specific species i
$I_T$=Ionic Strength as defined by G. N. Lewis
(Alkaline earth hypochlorites require a different expression for ionic strength to reflect complex multivalent ionic interactions.)

Because the Total Ionic strength represented by equation VI includes the concentrations of the anion and cation of the hypochlorite species, the total ionic strength is a function of the hypochlorite strength. If the ionic strength of the hypochlorite species is removed from the total ionic strength calculation then a new function called "residual ionic strength (RI)" is newly defined.

$RI$=Total Ionic Strength ($I_T$)−[Ionic strength of Hypochlorite species]

This new parameter "Residual Ionic Strength" is only dependent on:—
1) The purity of the reactants involved in its production
2) The type of anion bound to the alkali metal reactant, used in the salt metathesis reaction.
3) The solubility of the salt produced by the metathesis reaction.
4) The solubility of salts produced as by-products or impurities associated with the reactants of the metathesis reaction.

The term "Residual Ionic Strength" can therefore be used to define a new family of hypochlorite products, produced by metathesis, which have residual ionic strengths below 1.7 g mole/litre, which is the minimum residual ionic strength of traditional CAP hypochlorite.

The uncoated admix of the present invention provides a sodium hypochlorite solution that has a residual ionic concentration of less than about 1.7 molarity.

This embodiment defines a new family of aqueous hypochlorite products, including Li, Na, and K, defined by their exceedingly low residual ionic strengths, which contributes to improved stability and the associated lowest rate of disproportionation into chlorates and perchlorates. (See equations VII, and VIII)

Figure 2:
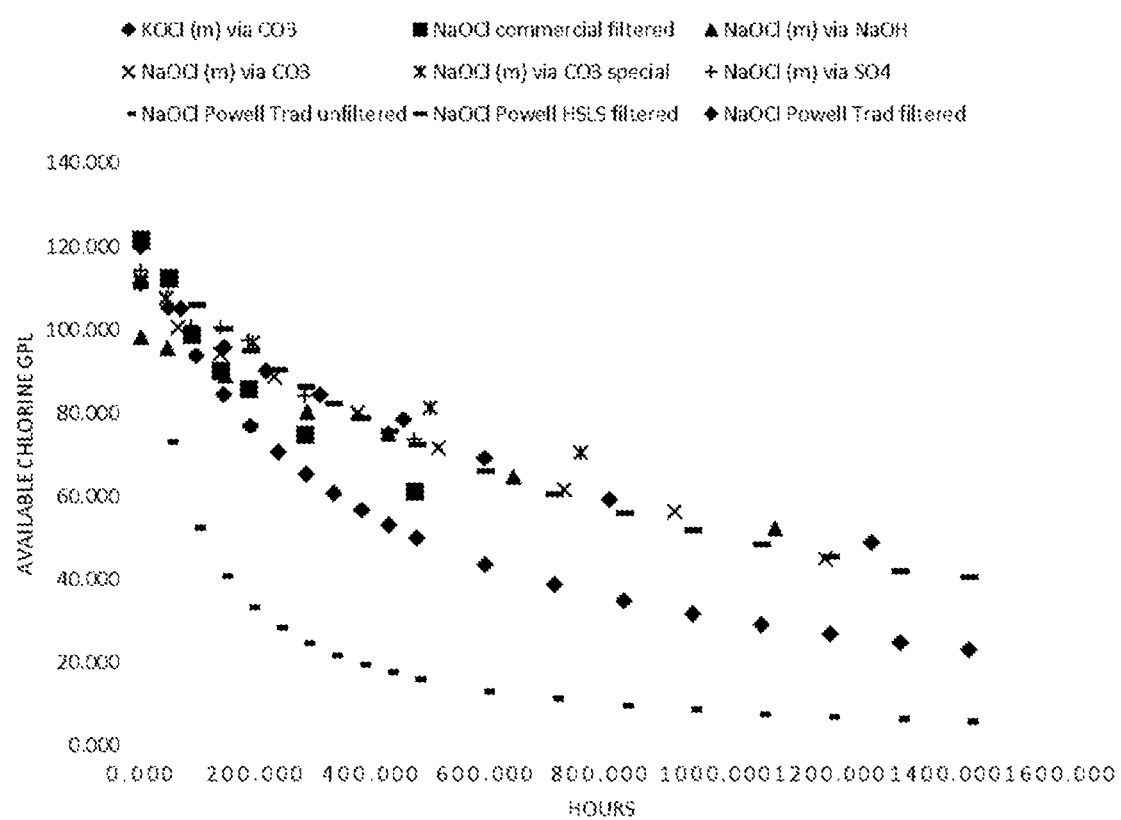
FIG. 2 illustrates a comparison of stabilities of hypochlorite solution of the present invention compared to other methods.
Figure 3:
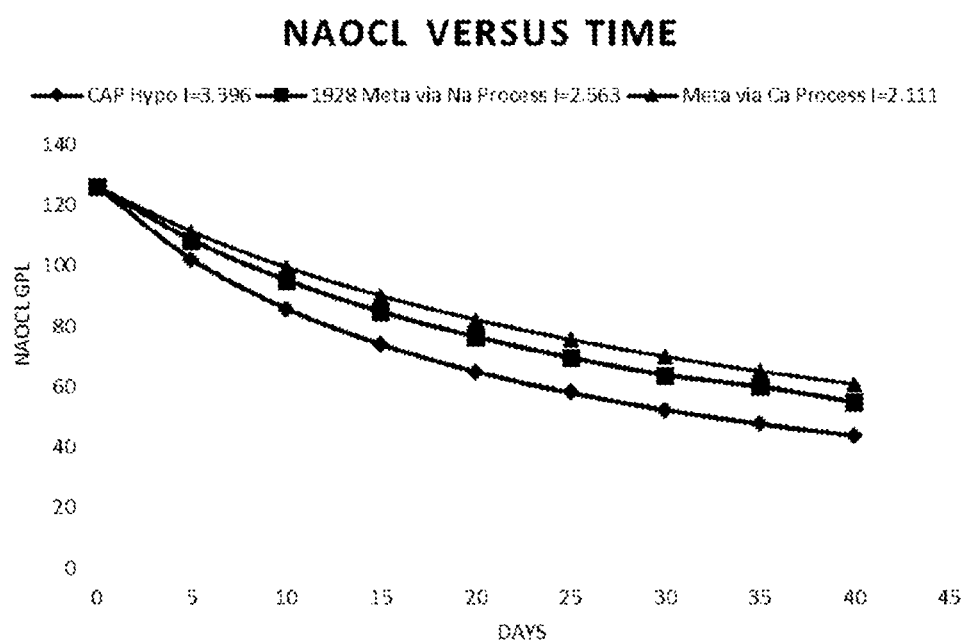
FIG. 3 illustrates the degradation of sodium hypochlorite solutions of the present invention compared to the CAP process.
Figure 4:
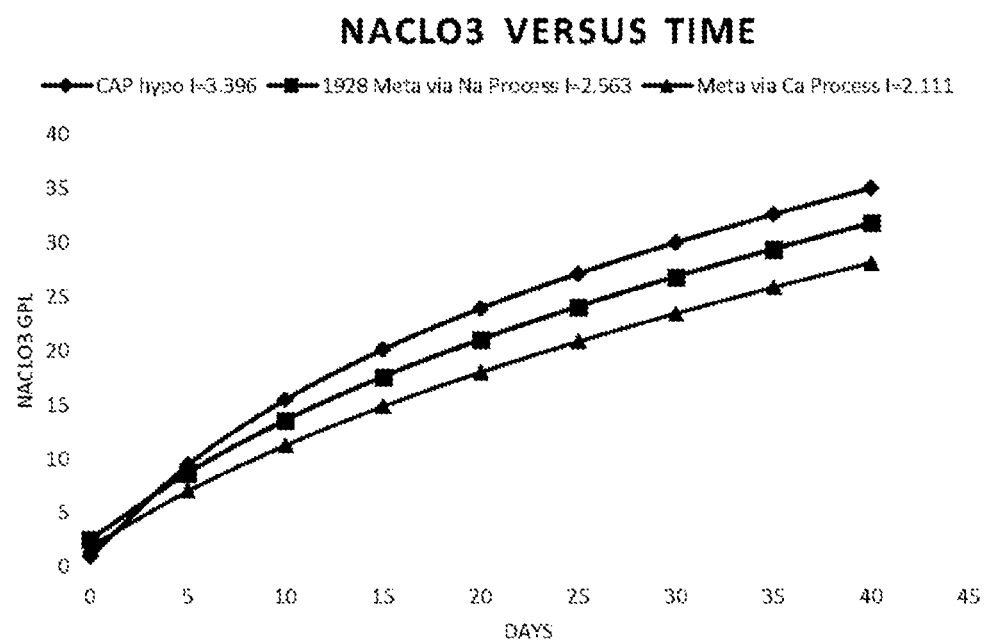
FIG. 4 illustrates the formation of chlorate from sodium hypochlorite solutions of the present invention compared to the CAP process.
Figure 5:
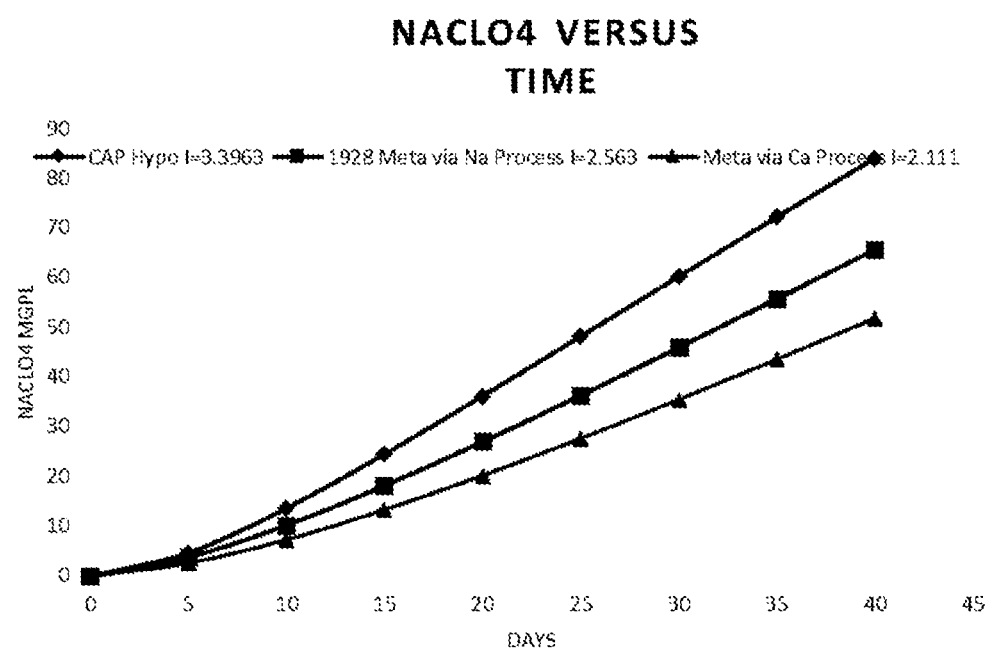
FIG. 5 illustrates the formation of perchlorate from sodium hypochlorite solutions of the present invention compared to the CAP process.
Figure 6:
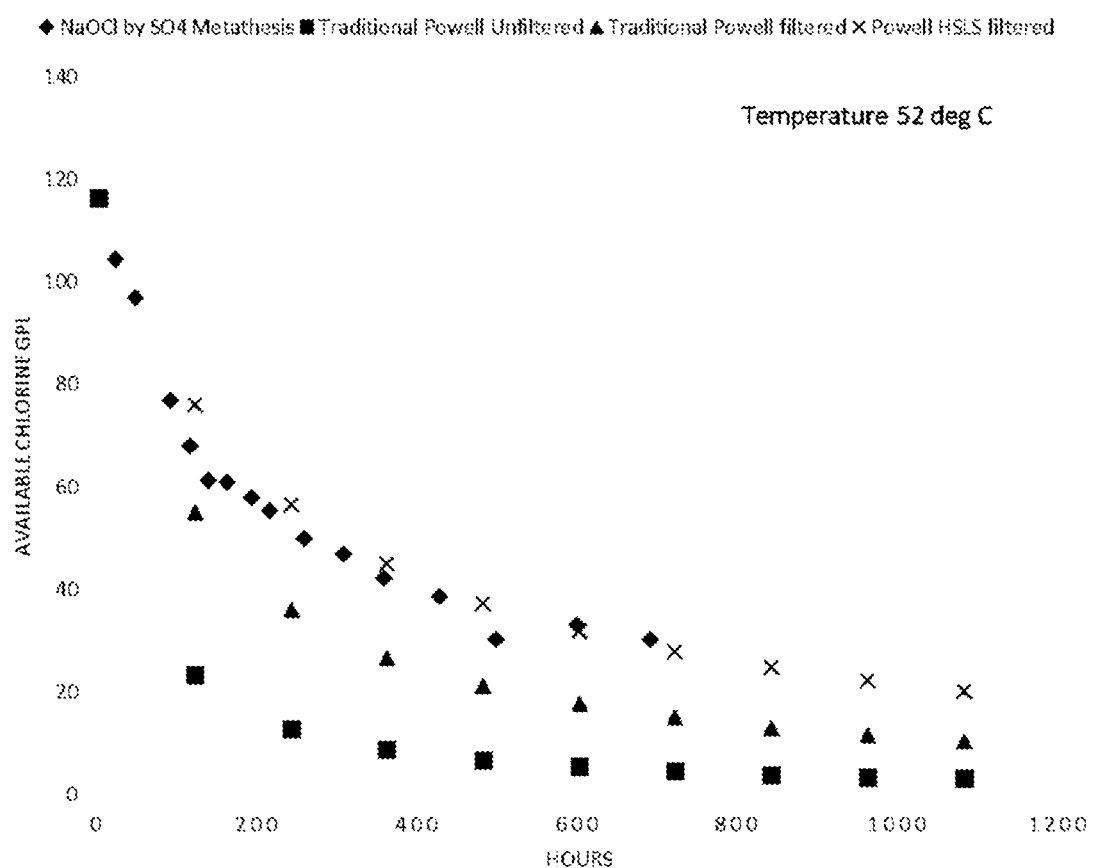
FIG. 6 illustrates a comparison of degradation of sodium hypochlorite solutions at 52° C.
Figure 7:
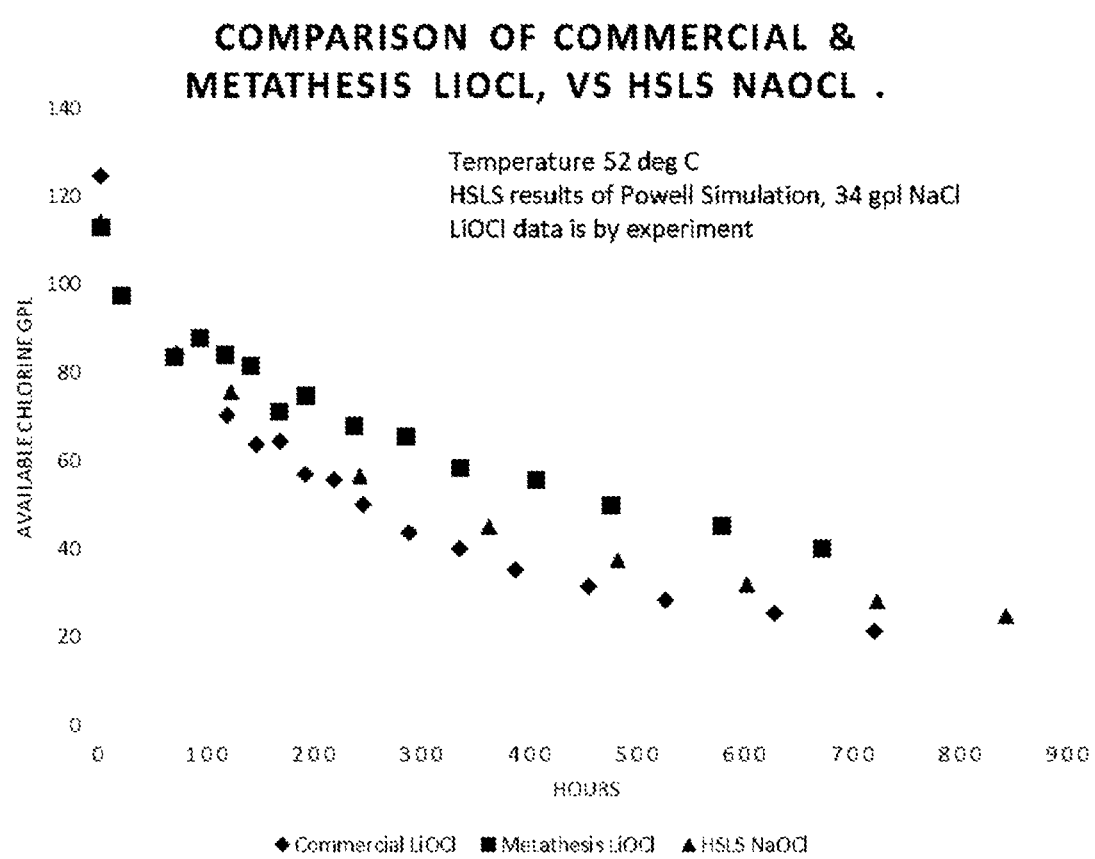
FIG. 7 illustrates a comparison of commercial and lithium hypochlorite solutions of the present invention, compared with simulation results of a high strength low salt (HSLS) sodium hypochlorite belonging to Powell Manufacturing.

The problem with the Chlor Alkali Process (CAP) for making hypochlorites Reaction (1) is product instability (due to amongst other things the co-generation of salt) and the associated generation of harmful by-products, such as chlorates and perchlorates. (see FIG. 2).

To mitigate this problem, hypochlorite solutions of the present invention are produced from a metathesis reaction. The hypochlorites produced by metathesis contain chlorate levels about 25% lower, and perchlorate levels about 50% lower than the equivalent CAP hypochlorite.

In some embodiments, the metathesized sodium hypochlorite solution has a residual ionic concentration less than about 1.7 molarity, down to about 0.2 molarity. In other embodiments, the residual ionic concentration is from about 0.2 M (g mole/l) to about 1.7 M. In other embodiments, the residual ionic concentration is from about 0.2 M to about 1.5 M, about 0.2 M to about 1.4 M, about 0.2 M to about 1.3 M or about 0.2 M to about 1.0 M.

A feature of this family of very stable aqueous hypochlorite products, which include LiOCl, KOCl and NaOCl, is their very low residual ionic concentrations. Residual Ionic concentrations as low as about 0.2 gm mole/litre, can be obtained by judicious choice of the alkali metal salt (or the equivalent hydrated alkali metal salt) used as a reactant.

In other embodiments, the sodium hypochlorite solution has a sodium hypochlorite concentration of up to about 15% w/v NaOCl.

Hypochlorites made by using Ca(OCl)$_2$ (Ca) which has been made by the calcium process, (reaction (V)) are more stable than products made by using Ca(OCl)$_2$ (Na) which has been made by the sodium process (reaction (IV)). (see FIG. 1).

TABLE 1

Common impurities in calcium hypochlorite produced by the sodium or calcium process, including the % w/w of available chlorine.

| Impurities | Sodium Process % w/w equation (IV) | Calcium Process % w/w equation (V) | Solubility (g/100 g in H$_2$O at 20° C.) |
|---|---|---|---|
| Available chlorine | 65-80 | 65 (minimum) | |
| Ca(OH)$_2$ | 5 (typical) | 6 (maximum) | 0.165 |
| CaCO$_3$ | 1 (typical) | 1 (typical) | 0.0014 |
| NaCl (soluble) | 20 (max) | 0 | 35.7 |
| CaCl$_2$ | 0 | 9 (maximum) | 74.5 |
| Ca(ClO$_3$)$_2$ | 0 | 1 (maximum) | (soluble) |
| H$_2$O | 10 (max) | 4 (max) | |
| MgCO$_3$ | Trace | Trace | 0.01 |
| Mg(OH)$_2$ | Trace | Trace | 0.0009 |
| BaCO$_3$ | Trace | Trace | 0.0022 |
| Ba(OH)$_2$ | Trace | Trace | 1.67 |

It is believed that the increased stability of aqueous metathesis hypochlorites formed from Ca(OCl)$_2$ (Ca) made by the calcium process is due to a smaller quantity of CaCl$_2$) in the product from the calcium process compared with the NaCl content of product from the sodium process. Further, the general insolubility of calcium impurities resulting in a purer aqueous hypochlorite and accordingly has a better aqueous stability as compared to the one made using the sodium process. A lower rate of formation of chlorate/perchlorate in the NaOCl made by Ca(OCl)$_2$ (Ca) as compared to that made by using Ca(OCl)$_2$ (Na), was also found.

In some embodiments, the admix is react-able in water to form a sodium hypochlorite solution and a salt. In other embodiments, the salt is insoluble in water. In this regard, the salt can be removed easily from the solution by filtration or by other known means.

Advantageously, this further improves the purity of the resultant sodium hypochlorite solution, which has better stability with respect to lower disproportionation rates into chlorate and/or perchlorate.

In some embodiments, the sodium hypochlorite solution has a concentration of less than 15% w/v, less than 20% w/v, less than 25% w/v, or less than 30% w/v.

The disproportionation products of hypochlorites are chlorates and perchlorates. The inventors have further investigated the hypochlorite, chlorate, perchlorate and O$_2$ content of the solution and determined that these concentrations are dependent on several factors such as temperature, starting chlorate, hypochlorite and ionic strengths. By regulating these factors, the disproportionation products of the composition can be controlled to a minimum, and when compared to hypochlorite produced by CAP and other commercially available solid such as LiOCl and Ca(OCl)$_2$ (made into aqueous solutions), the present family of hypochlorites show superior stabilities and hence less disproportionation (see FIG. 2).

Accordingly, the present invention also relates to an uncoated admix comprising:
a) calcium hypochlorite (Ca(OCl)$_2$) having an available chlorine content of from 65-80% and a water content of about 4% to about 10% w/w; and
b) a hydrated phase change material;
wherein the Ca(OCl)$_2$ and phase change material is physically and intimately mixed as a solid crystalline form in approximately stoichiometric proportions to form a tablet or a granular mix of solids;
wherein the hydrated phase change material is a hydrated alkali metal salt selected from hydrated Na$_2$CO$_3$, hydrated Na$_2$SO$_4$, hydrated Na$_3$PO$_4$, hydrated NaHCO$_3$, hydrated NaHSO$_4$, hydrated Na$_2$HPO$_4$ or hydrated NaH$_2$PO$_4$;
wherein the total water (H$_2$O in the PCM+ for instance, approximately 10% H$_2$O in Ca(OCl)$_2$) is about 30% w/w to about 45% w/w of the uncoated admix;
wherein the hydrated phase change material is about 55% w/w to about 70% w/w of the uncoated admix;
wherein the damp (eg approximately 10% H$_2$O), Ca(OCl)$_2$ is about 35% w/w to about 45% w/w of the uncoated admix;
wherein the uncoated admix has an available chlorine content of from 20-35%; wherein the uncoated admix is react-able in water to form a sodium hypochlorite solution with a concentration of less than 15% w/v and a salt; and
wherein the uncoated admix is classified as a non Division 5.1 oxidizer.

The present invention also relates to a sodium hypochlorite solution produced from the uncoated admix, the sodium hypochlorite solution having a half-life about 1.4 to about 1.7 times than that of Chlor Alkali Plant (CAP) hypochlorites under the same conditions of concentration, temperature profile, exposure to light, storage time and container material; the sodium hypochlorite solution having a chlorate concentration at least 25% less than that of CAP hypochlorites under the same conditions of concentration, temperature profile, exposure to light, storage time and container material;
the sodium hypochlorite solution having a perchlorate concentration at least 50% less than that of CAP hypochlorites under the same conditions of concentration, temperature profile, exposure to light, storage time and container material;
the sodium hypochlorite solution having a residual ionic concentration of less than 1.7 g moles/litre and preferably about 0.2 g moles/litre; and
the sodium hypochlorite solution having an available chlorine concentration of about 100 g/i to about 160 g/l.

The present invention relates to a hypochlorite solution produced by a reaction of calcium hypochlorite with a non-hydrated alkali metal salt;
wherein the calcium hypochlorite and the non-hydrated alkali metal salt (family includes Na, Li and K) are in approximately stoichiometric proportions;
wherein an anion associated with the non-hydrated alkali metal salt is selected from $CO_3^{2-}$, $SO_4^{2-}$, $PO_4^{3-}$, $HPO_4^{2-}$, $H_2PO_4^{2-}$, $OH^-$, $SO_3^{2-}$, $HSO_4^-$, $HSO_3^-$ and $S_2O_3^{2-}$;
the hypochlorite solution having a half-life about 1.4 to about 1.7 times than that of Chlor Alkali Plant (CAP) hypochlorites under the same conditions of concentration, temperature profile, exposure to light, storage time and container material;
the hypochlorite solution having a chlorate concentration at least 25% less than that of CAP hypochlorites under the same conditions of concentration, temperature profile, exposure to light, storage time and container material;
the hypochlorite solution having a perchlorate concentration at least 50% less than that of CAP hypochlorites under the same conditions of concentration, temperature profile, exposure to light, storage time and container material;
the hypochlorite solution having a residual ionic concentration of less than 1.7 g moles/litre and preferably about 0.2 g moles/litre; and
the hypochlorite solution having an available chlorine concentration of about 100 g/l to about 160 g/l.

In some embodiments, the calcium hypochlorite is produced from a reaction of chlorine and calcium hydroxide (calcium process). The sodium hypochlorite solution or hypochlorite solution can have a half-life about 20% to about 50% more than that of a hypochlorite solution produced from a reaction of calcium hypochlorite produced by the reaction of calcium chloride and sodium hypochlorite (sodium process).

In an embodiment, the admix further comprises a soluble alkali. The soluble alkali can be sodium hydroxide. Other alkali can be potassium hydroxide, calcium hydroxide or lithium hydroxide.

In another embodiment, the soluble alkali is present in an amount of about 0.1 g/L to about 0.5 g/L. In other embodiments, the concentration is about 0.1 g/L to about 0.4 g/L, about 0.1 g/L to about 0.3 g/L or about 0.1 g/L to about 0.2 g/L.

In another embodiment, the admix further comprises an alkaline buffer to the sodium hypochlorite, wherein the alkaline buffer is selected from carbonate, bicarbonate or a mixture thereof.

In other embodiments, the sodium hypochlorite solution or hypochlorite solution further comprises a soluble alkali of about 0.1 g/L to about 0.5 g/L, and optionally an alkaline buffer selected from carbonate, bicarbonate or a mixture thereof; and
wherein the sodium hypochlorite solution or hypochlorite solution is produced via a metathesis reaction.

In another embodiment, the composition is substantially free of impurities. This is especially so if the calcium hypochlorite made by calcium process is used.

In another aspect, the present invention provides an admix comprising:
a) calcium hypochlorite having an available chlorine content of from 65-80% and a water content of about 4% to about 10% w/w; and
b) a non-hydrated alkali metal salt;
wherein the admix is in a solid form,
wherein the mix of the non-hydrated alkali metal salt and calcium hypochlorite is in approximately stoichiometric proportions; and
wherein the admix is react-able in water to form a sodium hypochlorite solution and a salt.

The alkali metal can be selected from Na, Li or K.

In other embodiments, the anion associated with the alkali metal salt is selected from $CO_3^{2-}$, $SO_4^{2-}$, $PO_4^{3-}$, $HPO_4^{2-}$, $H_2PO_4^-$, $OH^-$, $SO_3^{2-}$, $HSO_4^-$, $HSO_3^-$ and $S_2O_3^{2-}$.

In another aspect, the present disclosure relates to a method for preparing an admix, including admixing a phase change material with calcium hypochlorite (having an available chlorine content of from 65-80% and a water content of about 4% to about 10% w/w), wherein the admix is in a solid form,
- wherein the phase change material is a hydrated alkali metal salt selected from hydrated $Na_2CO_3$, hydrated $Na_2SO_4$, hydrated $Na_3PO_4$, hydrated $NaHCO_3$, hydrated $NaHSO_4$, hydrated $Na_2HPO_4$ or hydrated $NaH_2PO_4$;
- wherein the mix of the phase change material to and the calcium hypochlorite is in approximately stoichiometric proportions;
- wherein the weight ratio of total water (for instance, approximately 10% with $Ca(OCl)_2$+PCM hydration) to the composition is about 30% w/w to about 45% w/w; and
- wherein the composition is react-able in water to form a sodium hypochlorite solution and a salt.

In an embodiment, the method for preparing a admix, includes mixing a phase change material with calcium hypochlorite;
- wherein the admix is in a solid form,
- wherein the phase change material is a hydrated alkali metal salt selected from hydrated $Na_2CO_3$, hydrated $Na_2SO_4$, hydrated $Na_3PO_4$, hydrated $NaHCO_3$, hydrated $NaHSO_4$, hydrated $Na_2HPO_4$ or hydrated $NaH_2PO_4$;
- wherein the (PCM) and the $Ca(OCl)_2$ are in approximately stoichiometric proportions; and
- wherein the weight ratio of total water (for instance, approximately 10% with $Ca(OCl)_2$+PCM hydration) to the admix is about 30% w/w to about 45% w/w; and
- wherein the admix is react-able in water to form a sodium hypochlorite solution and a salt.

In an embodiment, the phase change material is in a solid form. In another embodiment, the phase change material is provided as a pellet or a powder. Accordingly, the admix can be provided in a pelletised form, granules or as a tablet.

The uncoated admixes of the present invention may be used to make sodium hypochlorite within a device for chlorinating pools and spas (hot tubs) that generates the required sodium hypochlorite, in situ, without using liquefied chlorine or electrolysis.

In an embodiment the device is a floatable dispenser for sodium hypochlorite generation in situ.

While some existing devices deliver controlled quantities of pre-prepared biocides (eg calcium hypochlorite), none can generate sodium hypochlorite (non electrolytically) in situ.

Advantages of this device dispenser over existing common treatment methods:—

The floating sodium hypochlorite dispenser device disclosed herein has the following beneficial features:—
1. The customer doesn't have to handle the weight, and thus ergonomic strain, associated with liquid chlorine in large carboys (5 l, 12.5 l, 15 l, 20 L or 25 L). (Liquid Chlorine is 87.5% water). For instance, the admixes disclosed herein may be presented in water permeable sachets that are approximately $\frac{1}{10}^{th}$ the weight of the equivalent liquid chlorine.
2. Customers will only need to purchase the device dispenser once as its reusable.
3. The sachets containing the admix are safer to store at home than calcium hypochlorite since they will not self-react.
4. Retailers will also be relieved that there is a safer alternative to the storage and handling problems associated with liquid chlorine and calcium hypochlorite. (ie, avoiding problems with oxidizing and self-reacting properties)
5. The floating sodium hypochlorite dispenser device is safe and simple to use. It releases chlorine in a slow, controlled release manner thus preventing the potential safety risk of exposure to high strength (12.5%) hypochlorite solution.
6. Since liquid chlorine degrades over time, customers frequently find that the product they purchase is well below the strength shown on the label. (It loses its efficacy over time.)
7. Easier to control free chlorine levels to target level, based on set volume of disinfectant (number of sachets/tablets) per set volume of pool water compared with liquid dosing.

Figure 11:
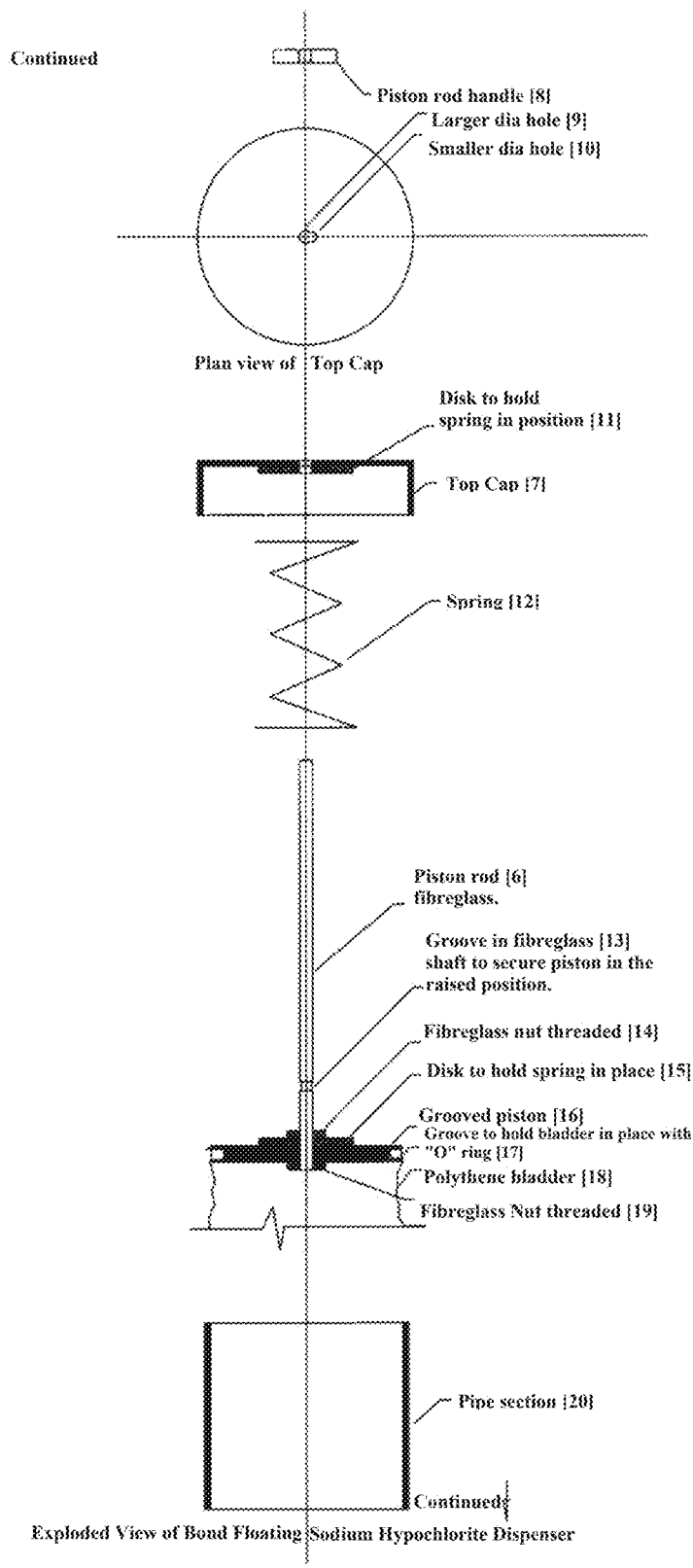
FIG. 11 illustrates an exploded CAD depiction of a floatable device suitable for dispensing the admix of the present invention into a pool or spa (hot tub).
Figure 12:
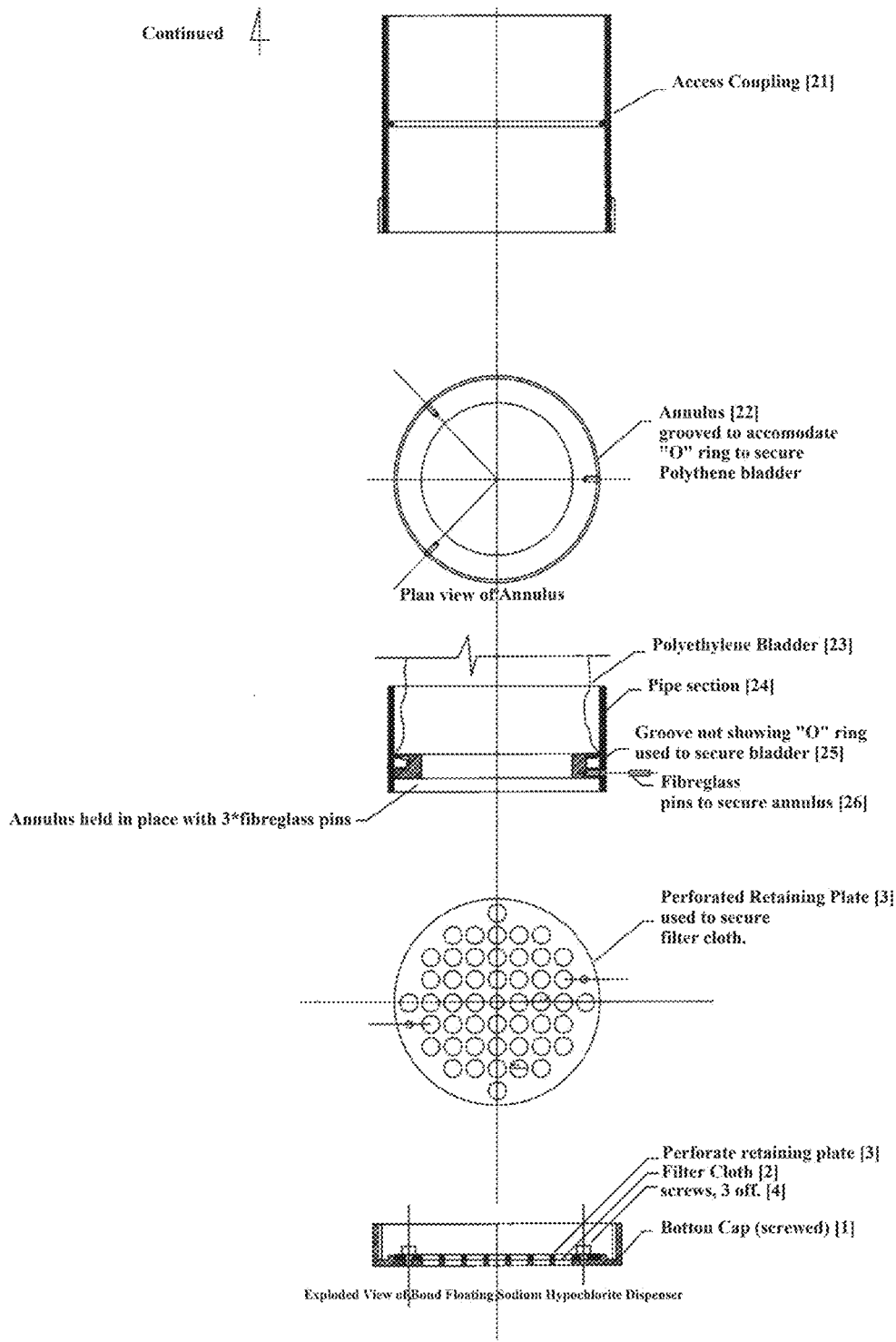
FIG. 12 illustrates further details of the exploded CAD of a part of a floatable device suitable for dispensing the admix of the present invention into a pool or spa (hot tub).
Figure 13:
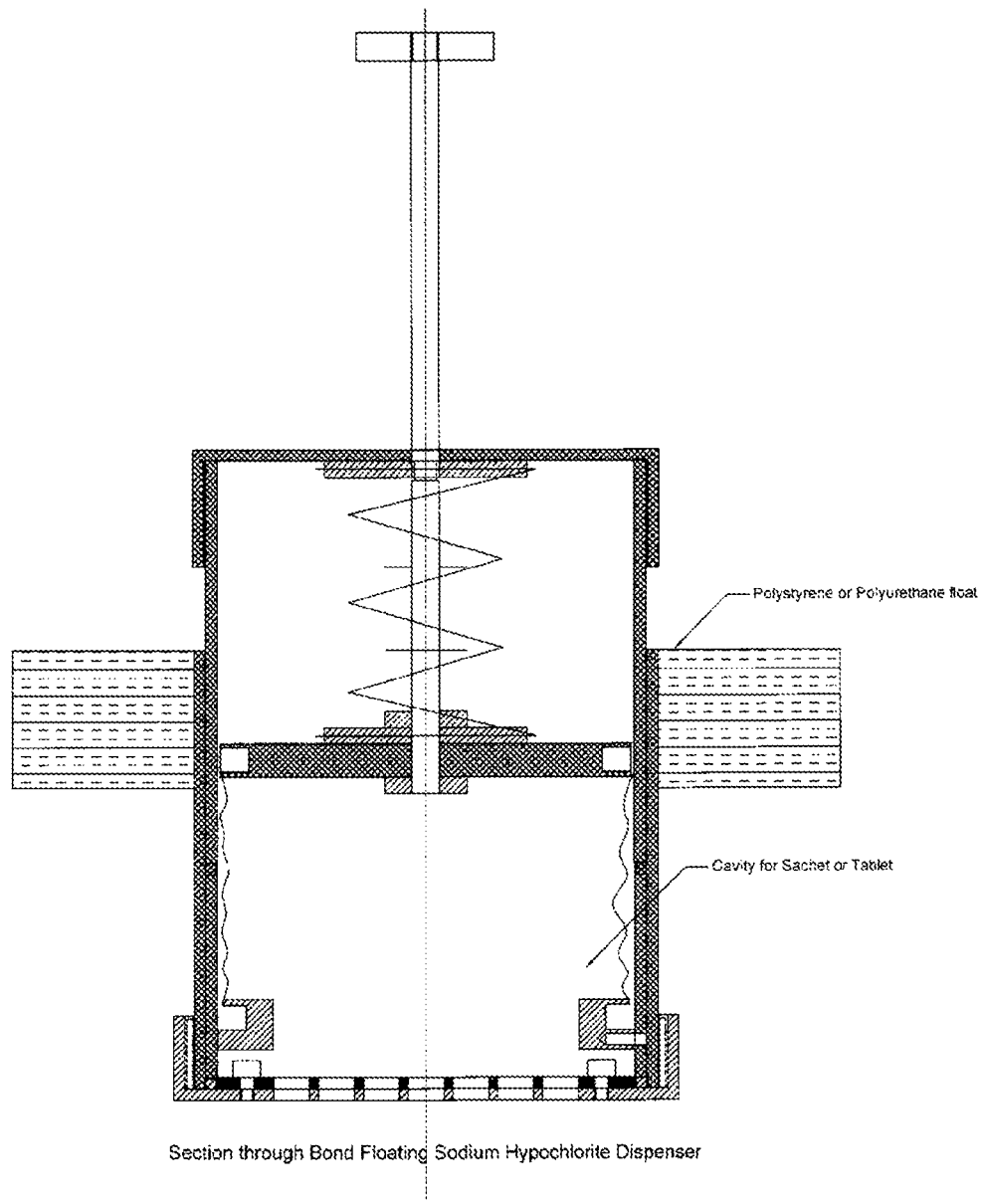
FIG. 13 illustrates a CAD of the assembled floatable device suitable for dispensing the admix of the present invention into a pool or spa (hot tub).

In an embodiment and with reference to FIGS. 11-13 the user may operate the device as follows:—
1. Remove the floating dispenser device from the pool.
2. Unscrew the bottom cap (1) and check that the filter cloth (2) is being held in place by the perforated retaining plate (3).
3. Check that the retaining plate (3) is securely attached to the bottom cap (1) by three screws (4).
4. Lift the plunger (5) and secure it in the compressed position by sliding the rod (6) into the specially shaped hole in the top cap (7).
5. Insert a sachet or tablet of admix into the bottom chamber of the dispenser device.
6. Replace the bottom cap (1) of the device.
7. Place the device into the pool with the rod (6) in the compressed position, and allow it to float overnight or for approximately 12 hours.
8. 12 hours later, release the rod (6). This will allow the spring to push the plunger down forcing the admix product through the filter cloth into the pool or spa.
9. When the rod (6) has fully travelled to the bottom of the device, while the device is still in the pool, work the rod (6) up and down in the device several times to pump pool water through the filter cloth (2). This will wash product from the solid residue collected on the filter cloth, and allow the device to be cleaned.
10. Remove the devise from the pool after use.
11. Remove the bottom cap (1) by unscrewing.
12. Remove and residual sachet material (eg plastic), wash in the pool and dispose to household waste.
13. Remove the accumulated solid residue from the perforated plate (3) and filter (2) by gently tapping the inverted bottom cap (1) over a household waste container. The rinsed solid may be disposed to the garden and buried if desired. Avoid contact with plants ($CaSO_4.2H_2O$ is a clay breaker, $CaCO_3$ is concentrated agricultural lime).
14. Rinse the bottom cap (together with attachments) in the garden. The device is now ready for recharging.

The above procedure can be repeated indefinitely as required to keep the pool or spa (hot tub) sanitized.

Accordingly, in another aspect the invention provides a kit of parts for pool or spa (hot tub) water sanitisation, comprising:

i) an uncoated admix as described above which is in tablet form or contained within a sachet; and ii) a floatable device characterised with a compartment (with a top and bottom) for housing the uncoated admix, wherein the top of the compartment is fitted with a plunging means which is designed to reduce the volume of the compartment when in use and wherein the bottom of compartment is fitted with a filtration means.

In an embodiment the filtration means is a plastic cloth with a weave that retains the finest (less than 1 micron) particles, for instance, the by-product insoluble salt $CaSO_4$, or $CaCO_3$.

In another aspect the invention provides a floatable device for pool or spa water sanitisation, said device characterised with a compartment comprising a top and bottom wherein the compartment has an internal volume for housing a pool or water sanitisation product in solid form, wherein the compartment is fitted with both one or more floatation means and the top of the compartment has a plunging means which is internally fitted within the compartment and is designed to reduce the volume of the compartment when in use, and wherein the bottom of compartment is fitted with a filtration means and is in fluid communication with the pool or spa (hot tub) water.

In an embodiment, the filtration means is a plastic cloth with a weave sufficient to remove particles of less than 1 micron.

It will be appreciated the pool or water sanitisation product may be the uncoated admix as disclosed herein and the product is in any solid form such that the product doesn't just escape from the compartment once the device is added to the pool. This ensures the generation of the sanitising hypochlorite (i.e., from reaction of the product with water) occurs over an extended period (eg over 12 hours such as discussed above). The solid may be as a tablet, or granules, or a solid form in a sachet, as discussed previously.

In another embodiment the filtration means is fitted to the bottom of the compartment by means of a screw cap arrangement such that the filtration means can be unscrewed from the compartment so as to fill the compartment with the desired amount of the solid sanitisation product. This arrangement is also advantageous as it allows the user to easily clean the filtration means after use or indeed replace, for instance, the plastic cloth which is the actual filter.

In another embodiment, the floatation device is attached to the outside of the compartment such that it enables the device to remain on the water surface and also serves to keep the filtration means in fluid communication with the water. In an embodiment then, it will be appreciated that the filtration means is submerged within the water while the top of the compartment remains above the surface.

In another embodiment the floatation means is a set of floatation wings which are composed of a material which floats (eg polystyrene, or polyurethane).

Advantageously, the admix can allow for the preparation of fresh hypochlorites at the point of use, such pool or spa (hot tub) water.

In another aspect, the present invention provides a method for preparing an admix, including mixing a non-hydrated alkali metal salt (family includes Na, Li and K) with calcium hypochlorite having an available chlorine content of from 65-80% and a water content of about 4% to about 10% w/w;
wherein the admix is in a solid form,
wherein the non-hydrated alkali metal salt and the calcium hypochlorite are in approximately stoichiometric proportions; and
wherein the admix is react-able in water to form a hypochlorite solution and a salt.

In an embodiment, the process further comprises a soluble alkali. The soluble alkali can be sodium hydroxide. Other alkali can be potassium hydroxide, calcium hydroxide or lithium hydroxide.

In another embodiment, the soluble alkali is present in an amount of about 0.1 g/L to about 0.5 g/L. In other embodiments, the concentration is about 0.1 g/L to about 0.4 g/L, about 0.1 g/L to about 0.3 g/L or about 0.1 g/L to about 0.2 g/L. Advantageously, the soluble alkali acts to further stabilise the hypochlorite solution.

In another embodiment, the process further comprises a step of adding an alkaline buffer to the sodium hypochlorite, wherein the alkaline buffer is selected from carbonate, bicarbonate or a mixture thereof.

In another embodiment, the metathesis reaction is performed at room temperature, or at about 1° C. to about 35° C.

In another aspect, the present disclosure relates to a metathesized metal hypochlorite solution, the metal hypochlorite solution having an residual ionic concentration less than 1.7 molarity, the metal hypochlorite solution having an available chlorine content of about 100 g/L to about 160 g/L; and
wherein the metal is selected from Na, K or Li.

In some embodiments, the metathesized hypochlorite solution has a residual ionic concentration less than about 1.7 molarity. In other embodiments, the residual ionic concentration is from about 0.2 M (g·mole/L) to about 1.7 M. In other embodiments, the residual ionic concentration is from about 0.2 M to about 1.6 M, about 0.2 M to about 1.5 M, about 0.2 M to about 1.4 M or about 0.2 M to about 1.2 M. In some embodiments, the hypochlorite solution has a residual ionic concentration of about 0.2 M to about 1 M.

Advantageously, the metathesized alkali metal hypochlorite solution has good aqueous stability compared to Chlor Alkali Plant (CAP) hypochlorite when exposed to the same conditions and at the same concentrations. For example, there is an approximately 25% reduction of chlorate when compared with CAP hypochlorite exposed to the same conditions and at the same concentrations.

Advantageously, the metathesized metal hypochlorite solution has approximately 50% reduction of perchlorate when compared with CAP hypochlorite exposed to the same conditions and at the same concentrations.

In other embodiments, the metathesized alkali metal hypochlorite solution comprises a soluble alkali of about 0.1 g/l to about 0.5 g/l. In other embodiments, the concentration is of about 0.1 g/l to about 0.4 g/l or about 0.2 g/l to about 0.4 g/l.

In other embodiments, the metathesized alkali metal hypochlorite solution comprises an alkaline buffer selected from a carbonate/bicarbonate mixture.

In other embodiments, the metathesized hypochlorite solution has a half life of at least 1.4 times greater than that of Chlor Alkali Plant (CAP) hypochlorites. Preferably, the half life is at least 1.7 time greater than that of CAP hypochlorites.

In other embodiments, the metathesized hypochlorite solution is produced from an alkali metal salt or its corresponding hydrated form.

In other embodiments, the anion associated with the alkali metal salt or its corresponding hydrated form is selected from $CO_3^{2-}$, $SO_2^-$, $P_4^{3-}$, $HPO_4^{2-}$, $H_2PO_4^-$, $OH^-$, $SO_3^{2-}$, $HSO_4^-$, $HSO_3^-$ and $S_2O_3^{2-}$.

It will be appreciated that many further modifications and permutations of various aspects of the described embodiments are possible. Accordingly, the described aspects are intended to embrace all such alterations, modifications, and variations that fall within the spirit and scope of the appended claims.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

EXAMPLES

1.

Figure 8:
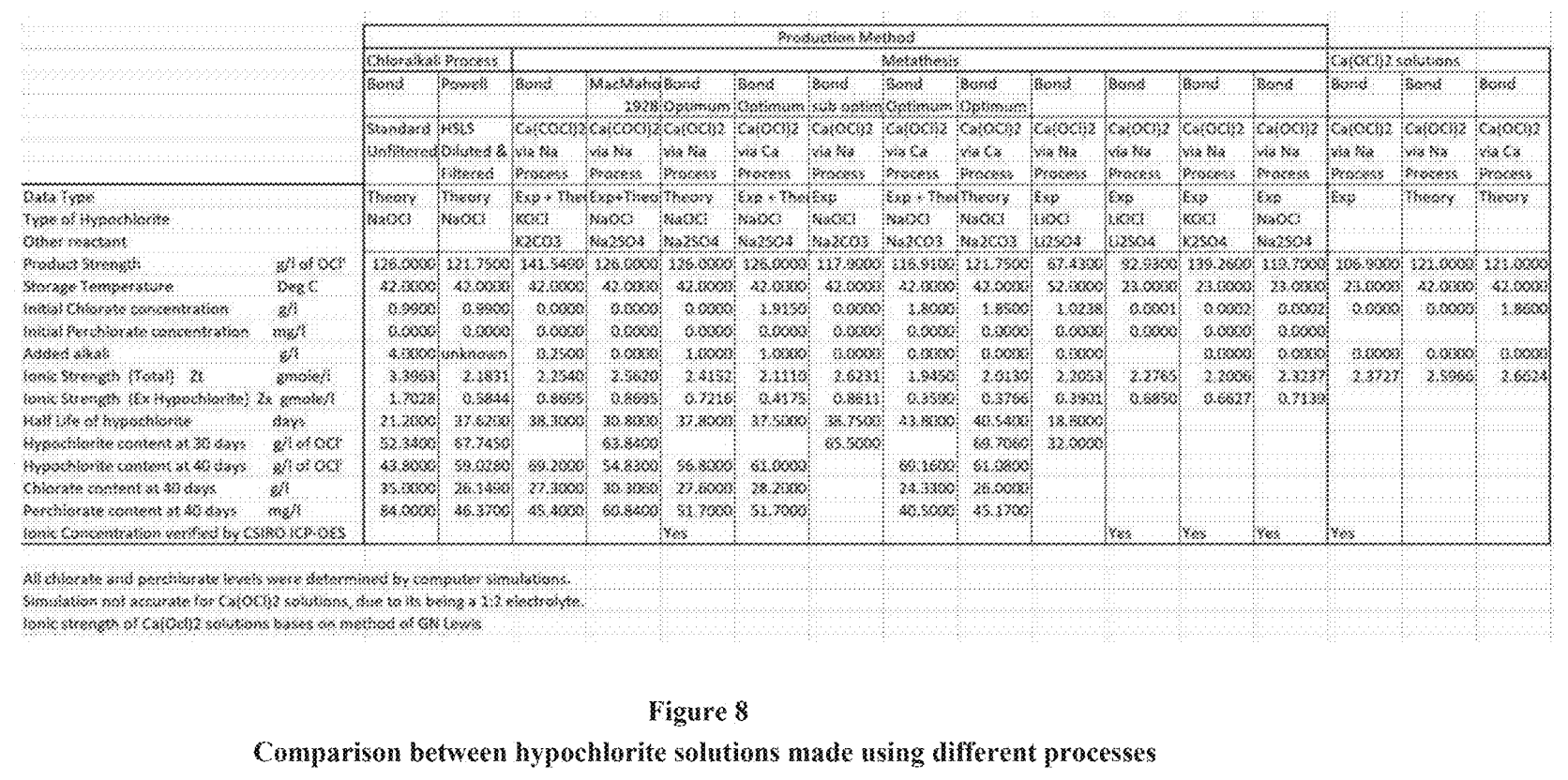

Chlorate, perchlorate and ionic concentrations of the hypochlorite composition of the present invention (Bond Chemicals Pty Ltd) are compared with other hypochlorite solutions in FIG. 8; which shows that production by selected metathesis reactions will produce the lowest perchlorate levels due to the lowest residual ionic concentrations.

2.

The economics (CAPEX and OPEX) associate with drinking water chlorination are detailed in FIG. 9; which again shows that the optimum methodology for water chlorination is by metathesis.

3.

The inventors have tested the reactivity of the solid hypochlorite admixes by contacting them with brake fluid. This provides a simple test for quick and reliable indication of reactivity. Selected examples were then tested under the UN Protocol to further confirm the results of the "brake fluid tests", are in line with the UN Protocol tests.

Materials used in Reactivity Testing are as follows:—
(Calcium Hypochlorite used was commercial HY-CLOR Supershock, 700 gm/kg of available chlorine.
Brake Fluid:—Ampol Dot 4 For Disc and Drum Brakes.
Examples of reduction in reactivity are disclosed in FIG. 10. The stoichiometric reaction mix of mono hydrated lithium sulphate and calcium hypochlorite showed some reactivity. This may be explained by the fact that the lithium sulphate used was not a deca or dodecahydrate; in fact $LiSO_4 \cdot H_2O$ is not listed as a PCM.

The tests show that the stoichiometric mixes of $Ca(OCl)_2$ with the decahydrates of sodium carbonate and sulphate and mixes of $Ca(OCl)_2$ with the hydrated salts of $Na_3PO_4$ and $Na_2HPO_4$ are Non 5.1 Oxidizers.

Two stoichiometric metathesis reaction mixes of:—
39.38% w/w $Ca(OCl)_2$ and 60.62% w/w $Na_2CO_3 \cdot 10H_2O$, and
36.58% w/w $Ca(OCl)_2$ and 63.41% w/w $Na_2SO_4 \cdot 10H_2O$, were found to not be classified as "Dangerous Good Division 5.1—Oxidizing Substances" when tested to the UN Protocol.

These findings will allow salt metathesis reaction admixes to be transported, stored, and handled, safely and cheaply without infringing severely limiting statutory regulations. The avoidance of these restrictions will allow the metathesis route for the formation of hypochlorites to be successfully commercialized.

4.

Studies are conducted on the stabilities of aqueous hypochlorites made by the following metathesis reactions as shown herein. The $Ca(OCl)_2$ was either obtained via the sodium or calcium process as shown by (Na) or (Ca).

$Na_2CO_3 + Ca(OCl)_2(Na) \rightarrow 2NaOCl + CaCO_3$ $Na_2CO_3 + Ca(OCl)_2(Ca) \rightarrow CaCO_3 + 2NaOCl$ $Na_2SO_4 + Ca(OCl)_2(Na) \rightarrow 2NaOCl + CaSO_4$ $Na_2SO_4 + Ca(OCl)_2(Ca) \rightarrow 2NaOCl + CaSO_4$ $Li_2SO_4 + Ca(OCl)_2(Na) \rightarrow CaSO_4 + 2LiOCl$ $K_2SO_4 + Ca(OCl)_2(Na) \rightarrow CaSO_4 + 2KOCl$ $K_2CO_3 + Ca(OCl)_2(Na) \rightarrow CaCO_3 + 2KOCl$ $2NaOH + Ca(OCl)_2(Na) \rightarrow Ca(OH)_2 + 2NaOCl$ For chlorate formation, the reaction rate expression is given by:—(Pisarenko, Gordon et al)

$$d(ClO_3^-)/dt = 3*K2[1/(3K2t+(OCl^-)^{-1})]^2 - K3(ClO_3^-)[1/(3K2t+(OCl^-)^{-1})] \quad (VII)$$

where $$\text{Log } K2 = 0.149*I + \log(2.083*10^{\wedge}10*T*\text{EXP}((-1.018*10^{\wedge}5)/(R*T))*\text{EXP}(-56.5/R))$$

Where I=total ionic concentration $$\text{Log } K3 = 0.0788*I + \log(2.084*10^{\wedge}10*T*\text{EXP}((-1.01*10^{\wedge}5)/(R*T))*\text{EXP}(-106/R))$$

Because the residual ionic concentration of all aqueous solutions of metathesis hypochlorites are less than those of the equivalent CAP hypochlorite, the rate of formation of $ClO_3$ will always be less.

For perchlorate formation, the reaction rate expression is given by:—(Pisarenko, Gordon et al)

$$d(ClO_4^-)/dt = K3*(ClO_3^-)*(OCl^-) \quad (VIII)$$

where K3 is provided above.

Because the residual ionic concentration of all aqueous solutions of metathesis hypochlorites are less than those of the equivalent CAP hypochlorite, the rate of formation of $ClO_4^-$ will always be less.

The reaction rate of $OCl^-$ is given by:—(Pisarenko, Gordon et al)

$$d(ClO^-)/dt = -3K2*(OCl^-)^2$$

where K2 was supplied previously.

Although the disproportionation of hypochlorite is second order with respect to the $OCl^-$ concentration, the plot of disproportionation versus time does not align with the rate equation supplied. The reason for this is that the disproportionation of hypochlorite occurs through two parallel paths, one to chlorate and the other to oxygen. The path to chlorate is then followed by a consecutive reaction to perchlorate. The final concentration of hypochlorite can only be ascertained by combining the rate equations and a mass balance.

The invention claimed is:

1. An uncoated admix comprising:
a) calcium hypochlorite ($Ca(OCl)_2$) having an available chlorine content of from 65-80% and a water content of about 4% to about 10% w/w; and b) a hydrated phase change material (PCM);

wherein the $Ca(OCl)_2$ and the hydrated PCM are physically and intimately mixed in approximately stoichiometric proportions to form a solid crystalline form;

wherein the hydrated PCM is a hydrated alkali metal salt selected from hydrated $Na_2CO_3$, hydrated $Na_2SO_4$, hydrated $Na_3PO_4$, hydrated $NaHCO_3$, hydrated $NaHSO_4$, hydrated $Na_2HPO_4$ or hydrated $NaH_2PO_4$; and wherein the uncoated admix is about 30% w/w to about 45% w/w water;

wherein the hydrated PCM is about 55% w/w to about 65% w/w of the uncoated admix;

wherein the $Ca(OCl)_2$ is about 35% w/w to about 45% w/w of the uncoated admix; and wherein the uncoated admix has an available chlorine content of from 20-35%.

2. The uncoated admix of claim 1, wherein the uncoated admix is reactable in water to form a sodium hypochlorite solution with a concentration of less than 15% w/v and a salt.

3. The uncoated admix of claim 1, wherein the calcium hypochlorite $(Ca(OCl)_2)$ has a water content of about 10% w/w.

4. The uncoated admix of claim 1, wherein the hydrated PCM is selected from hydrated $Na_2CO_3$, hydrated $Na_2SO_4$, hydrated $Na_3PO_4$, and hydrated $NaHCO_3$.

5. The uncoated admix of claim 1, wherein the approximately stoichiometric proportions are about 1:1 to about 1:1.5.

6. The uncoated admix of claim 1, wherein the approximately stoichiometric proportions are about 1:1 to about 1:1.4.

7. The uncoated admix of claim 1, wherein the total water is about 35% w/w to about 40% w/w of the uncoated admix.

8. The uncoated admix of claim 1, wherein the hydrated phase change material is about 60% w/w to about 65% w/w of the uncoated admix.

9. The uncoated admix of claim 1, further comprising an alkaline buffer.

10. The uncoated admix of claim 1, wherein the approximately stoichiometric proportions are about 1:1 to about 1:1.3.

11. The uncoated admix of claim 1, wherein the approximately stoichiometric proportions are about 1:1 to about 1:1.2.

12. The uncoated admix of claim 1, wherein the approximately stoichiometric proportions are about 1:1 to about 1:1.1.

13. The uncoated admix of claim 1, wherein the solid crystalline form is in the form of a tablet.

14. The uncoated admix of claim 1, wherein the solid crystalline form is in the form of a granular mix of solids.

15. A kit of parts for pool or spa (hot tub) water sanitisation, comprising:
   i) an uncoated admix claim 1, where the uncoated admix is in tablet form or contained within a sachet; and
   ii) a floatable device comprising a compartment for housing the uncoated admix, wherein a top of the compartment is fitted with a plunging means designed to reduce the volume of the compartment when in use and a bottom of the compartment is fitted with a filtration means.

* * * * *